United States Patent
Huang et al.

(10) Patent No.: US 9,134,259 B2
(45) Date of Patent: Sep. 15, 2015

(54) X-RAY SOURCE GRATING STEPPING IMAGING SYSTEM AND IMAGE METHOD

(75) Inventors: Zhifeng Huang, Beijing (CN); Zhiqiang Chen, Beijing (CN); Li Zhang, Beijing (CN); Yuanjing Li, Beijing (CN); Yuxiang Xing, Beijing (CN); Ziran Zhao, Beijing (CN); Yongshun Xiao, Beijing (CN); Liang Li, Beijing (CN); Fei Ding, Beijing (CN)

(73) Assignees: TSINGHUA UNIVERSITY, Beijing (CN); NUCTECH COMPANY LIMITED, Beijing (CN)

(*) Notice: Subject to any disclaimer, the term of this patent is extended or adjusted under 35 U.S.C. 154(b) by 362 days.

(21) Appl. No.: 13/641,542
(22) PCT Filed: Dec. 27, 2010
(86) PCT No.: PCT/CN2010/002174
§ 371 (c)(1), (2), (4) Date: Dec. 10, 2012
(87) PCT Pub. No.: WO2011/130896
PCT Pub. Date: Oct. 27, 2011

(65) Prior Publication Data
US 2013/0094625 A1 Apr. 18, 2013

(30) Foreign Application Priority Data
Apr. 19, 2010 (CN) .......................... 2010 1 0149869

(51) Int. Cl.
G01N 23/00 (2006.01)
G01N 23/04 (2006.01)
A61B 6/00 (2006.01)

(52) U.S. Cl.
CPC ............ *G01N 23/046* (2013.01); *A61B 6/4291* (2013.01); *A61B 6/484* (2013.01); *G01N 2223/419* (2013.01)

(58) Field of Classification Search
CPC ................. G01N 23/20075; G01N 2223/064; G01N 2223/1016; A61B 6/484; A61B 6/4291; G21K 2207/005
USPC ....................................................... 378/6, 87
See application file for complete search history.

(56) References Cited

U.S. PATENT DOCUMENTS

| 8,515,002 B2* | 8/2013 | Huang et al. ...................... 378/6 |
| 2007/0042418 A1* | 2/2007 | Yehiely et al. ................... 435/6 |

(Continued)

FOREIGN PATENT DOCUMENTS

| CN | 201191275 Y | 2/2009 |
| CN | 101495853 A | 7/2009 |

(Continued)

OTHER PUBLICATIONS

International Search Report in International Application No. PCT/CN2010/002174, dated Mar. 31, 2011.

*Primary Examiner* — Michael Maskell
(74) *Attorney, Agent, or Firm* — Marshall, Gerstein & Borun LLP

(57) ABSTRACT

An X-ray imaging system comprising: an X-ray source, a source grating, a fixed grating module and an X-ray detector, which are successively positioned in the propagation direction of X-ray; an object to be detected is positioned between the source grating and the fixed gating module; said source grating can perform stepping movement in a direction perpendicular to the optical path and grating stripes; wherein the system further comprises a computer workstation for controlling said X-ray source, source grating and X-ray detector so as to perform the following processes: the source grating performs stepping movement in at least one period thereof; at each stepping step, the X-ray source emits X-ray to the object to be detected, and the detector receives the X-ray at the same time; wherein after at least one period of stepping and data acquisition, the light intensity of X-ray at each pixel point on the detector is represented as a light intensity curve; the light intensity curve at each pixel point on the detector is compared with a light intensity curve in the absence of the object to be detected, a pixel value of each pixel point is calculated from change in said light intensity curve; an image of the detected object is reconstructed according to the calculated pixel value.

22 Claims, 4 Drawing Sheets

(56) References Cited

U.S. PATENT DOCUMENTS

| | | | |
|---|---|---|---|
| 2007/0042962 A1* | 2/2007 | Adams et al. | 514/15 |
| 2007/0054848 A1* | 3/2007 | Tohyama et al. | 514/12 |
| 2007/0059747 A1* | 3/2007 | Bastian et al. | 435/6 |
| 2009/0128830 A1 | 5/2009 | Kottler et al. | |
| 2009/0316857 A1* | 12/2009 | David et al. | 378/62 |
| 2010/0119041 A1* | 5/2010 | Ohara | 378/87 |
| 2010/0246765 A1* | 9/2010 | Murakoshi et al. | 378/62 |
| 2011/0293064 A1* | 12/2011 | Huang et al. | 378/6 |
| 2012/0224670 A1* | 9/2012 | Kiyohara et al. | 378/62 |
| 2012/0243658 A1* | 9/2012 | Geller et al. | 378/16 |

FOREIGN PATENT DOCUMENTS

| | | |
|---|---|---|
| CN | 101532969 | 9/2009 |
| JP | 2008145111 A | 6/2008 |

* cited by examiner

X-RAY SOURCE GRATING STEPPING IMAGING SYSTEM AND IMAGE METHOD

CROSS-REFERENCE TO RELATED APPLICATIONS

This is the U.S. national phase of International application No. PCT/CN2010/002174, filed Dec. 27, 2010, which claims the benefit of Chinese patent application No. 201010149869.4, filed Apr. 19, 2010.

TECHNICAL FIELD

The present invention generally relates to an X-ray imaging field, more specifically to projection imaging of an object using X-ray through a grating stepping technology.

BACKGROUND ART

In the prior art such as a CT scanning device, scan imaging of an object using X-ray has been widely used. Traditional X-ray scan imaging generally makes use of attenuation characteristics of the detected material to X-ray so as to examine the internal structure of the object in a nondestructive way. If the structural constitutions of respective parts inside the object are notably different in density, the effect of the traditional X-ray imaging technology is especially significant. As for substances consisting of light elements, they are weak-absorbing substances for X-ray, thus the internal specific structures thereof almost cannot be seen by means of the traditional X-ray imaging technology. It is also difficult to obtain a clear image even if other auxiliary means are used, such as injecting contrast agent into biological tissues, which results in a lot of imperfections. In the 1990s appeared an X-ray phase-contrast imaging technology. Said phase-contrast imaging is to observe change in the electron density inside an object by capturing phase-shift information of X-ray, thereby revealing the internal structure of the object. At the beginning, the appeared phase-contrast imaging methods usually enhance the low contrast resolution of the radiated image by using interference or diffraction phenomenon of coherent or partially coherent X-ray. On such a basis, in the patent applications CN200810166472.9 "System and method for X-ray gratings phase-contrast imaging" and CN200810224362.3 "X ray Phase contrast tomographic imaging", wherein all the contents of said patent applications are incorporated into the present application by reference, HUANG Zhifeng et al. put forward a novel technical concept and solution of non-coherent grating phase-contrast imaging, including: two absorption gratings are used to relatively move several steps in parallel in one grating period, the detector acquires one image at each step; after the acquisition process in one grating period has been finished, the information of the refracted image of the object to be detected is calculated by comparing the sample light intensity curve to which each pixel point corresponds with the background light intensity curve. This leads to a good phase-contrast imaging effect. Said method can be operated under multicolor, non-coherent ray sources to implement simple and feasible means.

In addition, during the progress of the X-ray imaging technology, there also appeared a dark-field imaging technology. Said dark-field imaging is a technology of imaging substance materials by using non-direct light such as scattered light, diffracted light, refracted light, fluorescent light, and the like, and imaging the internal structures of the substances by means of the difference in their capabilities of scattering X-ray. As for the dark-field imaging, due to the unique optical properties of hard X-ray, it is very difficult to produce the required optical elements, thus the hard X-ray dark-field imaging is always hard to achieve well. However, the hard X-ray dark-field imaging technology possesses particular advantages in the capabilities of distinguishing and detecting the microstructures insides the substances over the bright-field imaging and the phase-contrast imaging. Since scattering of the hard X-ray is of a micron-magnitude or even nanometer-magnitude, the hard X-ray dark-field imaging technology is able to see the ultrastructures inside the substances which cannot be distinguished in the hard X-ray bright-field imaging and phase-contrast imaging. Wherein in the patent application in 2009, CN200910088662.8 "X-ray dark-field imaging system and method", wherein all the contents of said patent application are incorporated into the present application by reference, HUANG Zhifeng et al. put forward a technical solution of performing dark-field imaging of an object by using X-ray, including: emitting X-ray to an object to be detected; enabling one of the two absorption gratings to perform stepping in at least one period; at each stepping step, the detector receiving X-ray and converting it into an electrical signal; after at least one period of stepping, the X-ray intensity at each pixel point on the detector is represented as a light intensity curve; calculating a secondary moment of the scattering angle distribution of each pixel according to the contrast between the light intensity curve at each pixel on the detector and the light intensity curve in the absence of the object to be detected; taking images of the object from different angles, and then obtaining a scattering information image of the object according to a CT reconstruction algorithm.

The grating imaging technologies as stated above all need to measure a light intensity curve of each detection unit (pixel point) on the detector by using the stepping technology, wherein the basic principle for the stepping technology is: after a source grating is fixed adjacently to an X-ray machine source, in the technology based on a Talbot-Lau interference method, a phase grating or parse grating relatively moves several steps in parallel in one grating period; however, in the technology based on a classic optical method, two absorption gratings relatively move several steps in parallel in one grating period. The detector acquires one image at each step. After finishing the acquisition process in one grating period, the refraction image information, attenuation image information and dark-field image information can be calculated by comparing the sample light intensity curve to which each pixel point corresponds with the background light intensity curve. Since the phase grating, parse grating or absorption grating has a period of a several-micron magnitude, and a stepping precision of a submicron-magnitude is required, which highly requires the precision of a mechanical device, the shock-proof of the integral device, and the environmental temperature, and the difficulty in constructing the imaging system and cost therefore extremely increases, thereby limiting application and extension of such a novel grating imaging technology.

SUMMARY OF THE INVENTION

With regard to the deficiencies in the prior art and on the basis that the technologies of X-ray grating phase-contrast imaging and dark-field imaging have been put forward, the present invention also provides an X-ray source grating stepping imaging system and method based on the X-ray grating imaging technology.

Specifically, the present invention provides an imaging system based on source grating stepping, wherein the stepping process is achieved only by moving a low-precision source grating, while a grating requiring high-precision is relatively fixed.

According to an example of the present invention, the X-ray imaging system comprises an X-ray source, a source grating, a fixed grating module and an X-ray detector, which are successively positioned in the propagation direction of X-ray; the object to be detected is positioned between said source grating and fixed grating module; said source grating may perform stepping movement in the direction perpendicular to the optical path direction and grating stripes; wherein said system may further comprise a computer workstation which controls said X-ray source, source grating, and X-ray detector, thereby implementing the following processes: said source grating performs stepping movement in at least one period thereof; at each stepping step, the X-ray source emits X-ray to an object to be detected, and the detector receives the X-ray at the same time; wherein after at least one period of stepping and data acquisition, the light intensity of X-ray at each pixel point on the detector is represented as a light intensity curve; the light intensity curve at each pixel point on the detector is compared with that in the absence of the object to be detected; a pixel value of each pixel point is calculated from change in said light intensity curve.

Wherein, said system further comprises an actuation means for enabling the source grating to perform stepping movement, and/or enabling the object to be detected to rotate by an angle relative to other parts of the system under the control of the computer workstation. The stepping process of the source grating is repeated at each rotation angle, thereby obtaining X-ray imaging pixel values at multiple angles, and then a stereo image of the detected object is reconstructed according to a predetermined CT image reconstruction algorithm.

Wherein, said computer workstation comprises a data processing module for processing data information and obtaining pixel values of the respective points on the object to be detected upon calculation; an image reconstruction module for reconstructing an image of the detected object according to the pixel values obtained upon calculation; and a control module for controlling operations of the X-ray source, source grating, X-ray detector and data processing unit. Wherein, according to an example, said data processing module and said control module can be integrated and implemented by a general or dedicated processor.

In addition, said computer workstation further comprises a display unit for displaying the image of the detected object. In the case that many kinds of images can be obtained simultaneously, these images can be complementally displayed.

According to an example of the present invention, said computer workstation is capable of calculating refraction information of X-ray at a predetermined point on the object to be detected upon comparison between the light intensity curve in the presence of the object to be detected and the background light intensity curve in the absence of the object to be detected, and calculating a corresponding pixel value therefrom.

According to another example of the present invention, said computer workstation is capable of calculating scattering information of X-ray at a predetermined point on the object to be detected upon comparison between the light intensity curve in the presence of the object to be detected and the background light intensity curve in the absence of the object to be detected, and calculating a corresponding pixel value therefrom.

According to yet another example of the present invention, said computer workstation is capable of calculating attenuation information of X-ray at a predetermined point on the object to be detected upon comparison between the light intensity curve in the presence of the object to be detected and the background light intensity curve in the absence of the object to be detected, and calculating a corresponding pixel value therefrom.

According to another aspect of the present invention, it relates to an X-ray imaging method for imaging an object by using an X-ray imaging system, wherein said X-ray imaging system is as stated above, wherein said method comprises the following steps:

emitting X-ray to the object to be detected; enabling the source grating to perform stepping movement in at least one period; the X-ray detector receiving X-ray at each stepping step and converting it into a processable digital electrical signal; wherein, after at least one period of stepping and data acquisition, the X-ray light intensity at each pixel point on the detector is represented as a light intensity curve; the data processing module comparing the light intensity curve at each pixel point on the detector with the light intensity curve in the absence of the object to be detected, thereby obtaining change in the light intensity curve; calculating the pixel value at each pixel point on the detector from said change in the light intensity curve; and the image reconstruction module reconstructing the pixel values of the detected object as an image thereof.

Further, according to the examples of the method of the present invention, in said method the object to be detected is rotated, said respective steps are repeated at each rotation angle to obtain the distribution of pixel values of respective points of the object to be detected on the X-ray detector at multiple angles, and a stereo image of the object to be detected is then reconstructed according to the CT image reconstruction algorithm.

According to an example of the method of the present invention, it comprises calculating refraction information of X-ray at a predetermined point on the object to be detected upon comparison between the light intensity curve in the presence of the object to be detected and the background light intensity curve in the absence of the object to be detected, and calculating a corresponding pixel value therefrom. Or, according to another example, it comprises calculating scattering information of X-ray at a predetermined point on the object to be detected from comparison between the light intensity curve in the presence of the object to be detected and the background light intensity curve in the absence of the object to be detected, and calculating a corresponding pixel value therefrom. Or, according to yet another example, it comprises calculating attenuation information of the X-ray at a predetermined point on the object to be detected from comparison between the light intensity curve in the presence of the object to be detected and the background light intensity curve in the absence of the object to be detected, and calculating a corresponding pixel value therefrom.

According to the system or method of the present invention, it can be combined with several imaging mechanisms including attenuation imaging, dark-field scattering imaging and phase-contrast imaging, which display complementally and can be synthetically applied to the field such as material science, medical imaging of tissues (such as galactophore).

At the same time of obtaining the same image quality and effect, the present invention significantly reduces the high requirements of the existing technologies on the high-precision mechanical and movement devices, shock-proof devices, etc., thereby greatly reduces the device construction cost and makes the stability of the system notably increased, which thus makes it technically easy to apply the grating-based information synthetical imaging technology to the actual products such as medical devices.

SPECIFIC EMBODIMENTS

Figure 1:
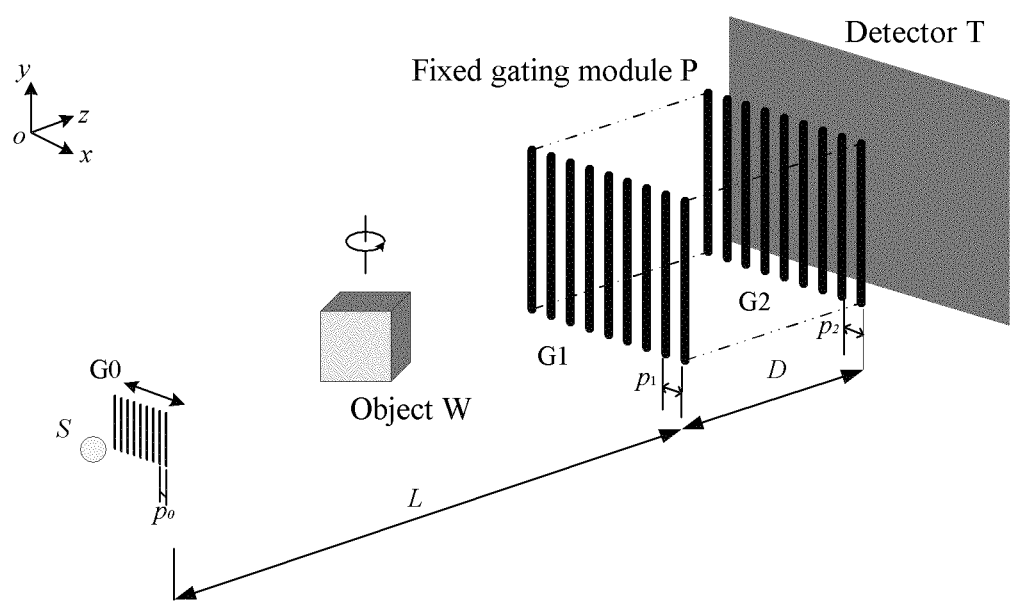
FIG. 1 is a schematic diagram of an X-ray imaging system of the present invention.

As shown in FIG. 1, according to the principle of the present invention, an X-ray imaging system essentially consists of: an X-ray machine S, a movable source grating G0, a fixed grating module P (including a first grating G1 and a second grating G2), and an X-ray detector T, which are successively positioned in the propagation direction of the emitted X-ray. An object to be detected is positioned between said source grating G0 and said fixed grating module.

Wherein the X-ray machine serving as an X-ray source may be a general X-ray machine used in current medical devices, which is usually a high-current pulse-mode X-ray machine suitable for imaging galactophore and may comprise corresponding auxiliary devices. The X-ray machine is used for emitting X-ray beams to the object to be detected. Generally speaking, the auxiliary devices include a filter. A medical X-ray machine has a working voltage usually set between 5 and 160 kVp. The X-ray beams emitted by the general X-ray machine may be fan beams, cone beams or parallel beams. In the present invention, cone beams are preferred.

Wherein the X-ray detector T is used for receiving X-ray and converting the received X-ray signals into electrical signals that digitally processable through a photoelectric signal conversion technology (such as digitized photography). Preferably, said detector may be a matrix detector, wherein each detection unit (pixel) may detect change in the intensity of the X-ray emitted on said unit. Preferably, said detector is capable of periodically acquiring and converting the X-ray. Preferably, a medicinal low-noise plane-array detector may be used, the plane-array detector with a dynamic range greater than 12 bit covers the entire imaging area. In order to detect calcified galactophore tissues of hundreds of microns, the spatial resolution of the detector is required to be about or below hundreds of microns (such as 70-100 microns).

In addition, said X-ray imaging system further comprises a computer workstation. The control of the entire imaging system, data transmission, image reconstruction and data processing can be accomplished by the computer workstation. The scan control information, position information, and projection data are input into the computer workstation via a data acquisition system. It is the workstation that accomplishes extraction of many kinds of information of the object, data preprocessing of the object and image reconstruction, and finally displays them on a display.

The computer workstation may comprise a data processing module which is set to calculate change in the light intensity (curve) after the X-ray passes through the object to be detected according to the digitally processable electrical signals output from the detector, and calculate the absorption information, scattering information or refraction information to the X-ray at a certain point on the object to be detected according to the change in said light intensity (curve), and calculate the pixel information of the object to be detected by using said information. These functions can be practically achieved by programmed software, or alternatively, theoretically achieved by a dedicated hardware chipset.

Further, the computer workstation may further comprise a control module (not shown in FIG. 1) for controlling the operations, such as relative rotation, stepping movement, X-ray emission and information acquisition, of the X-ray machine, source grating, object to be detected, fixed grating, detector and the like. Preferably, said control module and said data processing module can be integrated and implemented by a single general or dedicated processor.

Further, the computer workstation may comprise an imaging module (not shown in FIG. 1) for reconstructing an image of the object to be detected according to the obtained pixel information, outputting and displaying it. Wherein said reconstruction functional module may be implemented by the processor that also serves as the data processing module.

Said imaging system may further comprise an actuation means for enabling the source grating to perform stepping movement, and/or enabling the object to be detected to rotate by an angle relative to other parts of the system under the control of the computer workstation. The stepping process of the source grating is repeated at each rotation angle, thereby obtaining X-ray imaging pixel values at multiple angles, and then a stereo image of the detected object is reconstructed according to a predetermined CT image reconstruction algorithm. Said actuation means is defined here as a structure having a means for relatively rotating the object to be detected and having a function of enabling the source grating to perform stepping movement, which actually can be separately represented.

Further, the computer workstation may comprise a display unit for displaying the reconstructed image, which can be implemented by a general display.

The following text further describes the constituent parts having differences from the cited prior art and in need of particular introduction.

Fixed Grating Module

The fixed grating module P consists of two high-precision gratings G1 and G2. In the grating imaging technologies in the patent applications cited in the Background Art part, the two high-precision gratings as used need to perform relative stepping movement so as to realize the stepping technology; while in the present invention, the relative position thereof is constant and unchanged. The periods of the two gratings G1 and G2 are respectively set as $p_1$ and $p_2$, which are successively positioned in the emission direction of the X-ray beam in parallel.

Wherein, preferably, the periods of said two gratings are usually between 0.1 and 30 microns. The gratings use heavy metals as an absorption material, taking gold (Au) as an example, the height of gold is between 10 and 100 microns, decided by the energy of the X-ray as used. For example, as for the X-ray of 20 keV, the gold with a height greater than 10 microns can block 90% of the X-ray.

Wherein, the coherent condition of the X-ray is defined as $1_{coh}=(L\lambda/S')>p_1$ according to the physical principle, wherein $1_{coh}$ is a lateral coherent length, L is a distance from the source grating to the first grating G1 in the fixed grating module, S' is a width of the linear light source, X is a wavelength of the X-ray, and $p_1$ is a period of the first grating G1 in the ray direction.

In practice, there may be two circumstances:

1) When the imaging system satisfies said coherent condition, said first grating G1 is a phase grating and changes the phase of the incident X-ray, Talbot effect occurs behind the first grating G1. The second grating G2 serves as an absorption grating, which is parallelly placed in the Talbot distance diffracted by the first grating. The first and second gratings are relatively fixed.

2) When the imaging system does not satisfy said coherent condition, the two gratings G1 and G2 are both absorption gratings. The two absorption gratings are apart by a distance D and fixedly placed in parallel.

In one preferred example of the present invention, the imaging system does not satisfy the above-mentioned coherent condition, namely the X-ray used by the fixed grating module is non-coherent light, then the fixed grating module P adopts the setting under the second circumstance as stated above, the first and second gratings G1 and G2 are apart by a distance D.

Alternatively, in another example of the present invention, the imaging system satisfies the above-mentioned coherent condition, namely the X-ray used by the fixed grating module is coherent light or partially coherent light, then the fixed grating module P adopts the setting under the first circumstance as stated above, wherein the second grating G2 and the first grating G1 has a distance of Talbot distance $D_T$, and $D_T = p_1^2/(8\lambda)$.

Source Grating and Stepping Technology Thereof

A source grating G0 is a multi-slit absorption grating, which has the function of dividing the X-ray machine into a plurality of narrow-beam linear light sources. As shown in FIG. 1, in the present invention, the source grating is to achieve parallel movement in at least one grating period $p_0$ in the X direction that is perpendicular to the optical path direction (Z axis) and the grating stripe direction (Y direction), namely achieving stepping technology. In contrast, in the existing grating imaging technology, the position of the source grating is set to be fixed, or directly etched in the target material of the X-ray machine. As a result, it is the stepping of the source grating that distinguishes the present invention from the cited prior art. The period $p_0$ of the source grating is generally about a dozen of microns or dozens of microns, thus the step length of the stepping may be of a magnitude of several microns or a dozen of microns, even of a magnitude of dozens of microns, then a translation device has a precision of about several microns or a dozen of microns. It can be proved that the result of the source grating stepping technology may achieve an equivalent result as the relative stepping of two gratings of the grating module P in the prior art.

Figure 3:
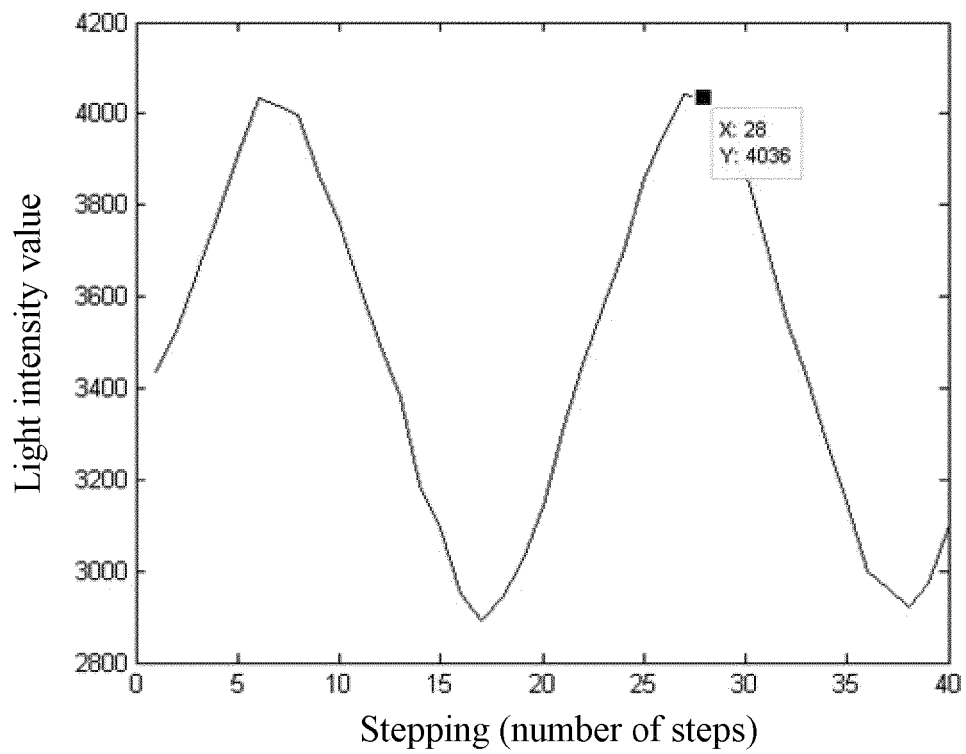
FIG. 3 shows a light intensity curve (background displacement curve) measured at a certain detection unit (pixel point) of an X-ray detector.

The curve of change in the intensity of X-ray received at a certain pixel point on the detector may be obtained through relative stepping movement of the source grating. As for the system shown in FIG. 1, the two gratings (G1, G2) of the fixed grating module are relatively fixed, while the source grating performs stepping along the X direction. When the source grating G0 is translated for one step, the detector can acquire data for one time; after N images are acquired within the translation distance range, a distribution of the curve of change in light intensity for each pixel (each point on the detection surface of the detector) on the detector in one grating period can be obtained. As shown in FIG. 3, the shape of function of change in light intensity is similar to a sinusoidal or cosinusoidal function, which is represented here by a continuous simulated curve and actually can be simulated by multiple points.

Source Grating Stepping Movement Process

Figure 2:
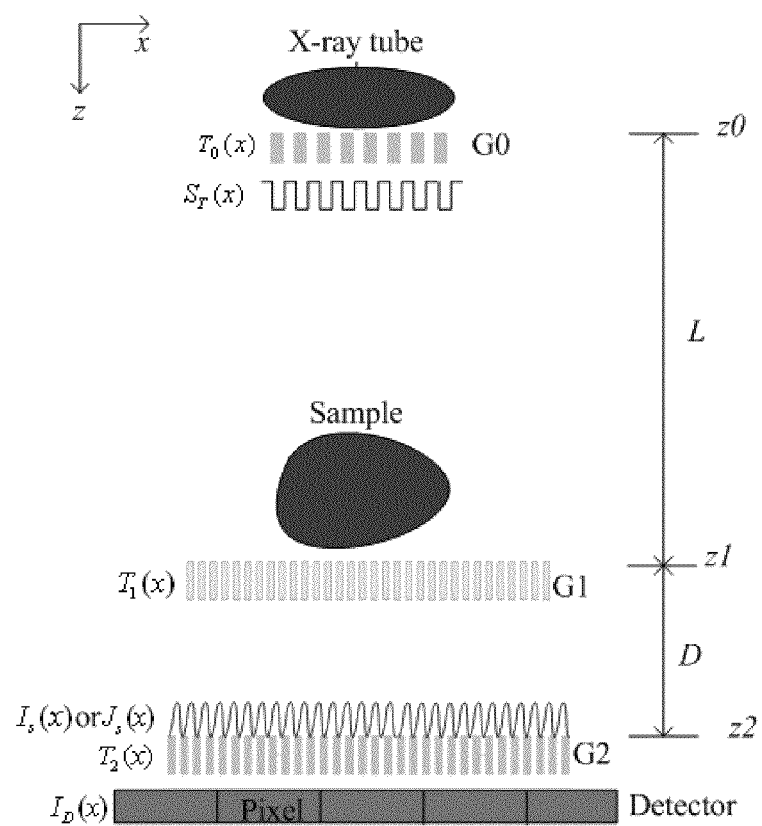
FIG. 2 is a schematic diagram of the imaging principle of the system of the present invention based on a movable source grating.

As shown in FIG. 2, an ideal condition is supposed to simplify calculation, namely the three gratings all have a size large enough in the X direction as shown. Wherein the source grating G0 divides the large-focus X-machine into a row of linear light sources, the distribution thereof is represented by the function $T_0(x)$. While the gratings G1 and G2 are respectively represented by $T_1(x)$ and $T_2(x)$. The periods of the gratings G0, G1 and G2 are $p_0$, $p_1$ and $p_2$.

The imaging principle of the source grating stepping is now explained by taking non-coherent X-ray imaging as an example, wherein the distance between the first grating G1 and the second grating G2 is D.

When the object to be detected is not placed in the optical path, an image formed at the position of the grating G2 by the grating G1 under the irradiation of X-ray is represented by the function $I_s(x)$, namely $$I_s(x) = I_1(x) * S(x) \quad (1)$$

wherein $I_1(x)$ is an image formed at the position of the grating G2 by the grating G1 under the irradiation of a point source, $S(x)$ is a projected image of the source grating G0 at the position of the grating G2, then $$I_1(x) = T_1\left(\frac{L}{L+D}x\right)$$

$$S(x) = S_T\left(-\frac{L}{D}x\right)$$

Wherein $S_T(x)$ is the light intensity distribution behind the grating G0, which is effected by both the X-ray source distribution function $S_0(x)$ and the transmittance function $T_0(x)$ of the grating G0, namely $S_T(x) = S_0(x)T_0(x)$.

It is noted that the periods of $I_1(x)$ and $S(x)$ at the position of G2 are equal to the period of the grating $T_2(x)$, which are all p2 and all marked as p for convenience.

The light intensity distribution function as detected by the detector is set as $I_D(x)$, then $$I_D(x) = I_s(x)T_2(x) \quad (2)$$

Since the size of the detector unit (pixel) is much larger than the period of the grating G2, the light intensity value received by a certain pixel is an accumulation of light intensity in the range of several or dozens of grating periods, thus it does not lack generality, it is set that $$I_1(x) = T_1\left(\frac{L}{L+D}x\right) = \sum_n a_n e^{2\pi i \frac{n}{p}x}$$

$$T_2(x) = \sum_n t_n e^{2\pi i \frac{n}{p}x}$$

$$S(x) = S_T\left(-\frac{L}{D}x\right) = S_0'(x)T_0'(x) = S_0\left(-\frac{L}{D}x\right)T_0\left(-\frac{L}{D}x\right)$$

-continued wherein $$S'_0(x) = S_0\left(-\frac{L}{D}x\right), T'_0(x) = T_0\left(-\frac{L}{D}x\right) = \sum_n f_n e^{2\pi i \frac{n}{p}x}$$

namely $$S(x) = S'_0(x)T'_0(x) = S'_0(x)\left[\sum_n f_n e^{2\pi i \frac{n}{p}x}\right] \approx \sum_n f'_n e^{2\pi i \frac{n}{p}x}$$

wherein, $a_n$, $t_n$ and $f_n$ are Fourier coefficients. $f'_n$ is a Fourier coefficient in consideration of the light source distribution.

When the source grating performs stepping, the displacement distance is set as $\chi$, the light intensity curve function (named background displacement curve) obtained in the detector unit is:

$$I_D(x, \chi) = I_s(x, \chi)T_2(x) = [I_1(x) * S(x+\chi)]T_2(x) \quad (3)$$

$$= \left[\left(\sum_n a_n e^{2\pi i \frac{n}{p}x}\right) * \left(\sum_m f'_m e^{2\pi i \frac{m}{p}(x+\chi)}\right)\right]\left(\sum_k t_k e^{2\pi i \frac{n}{p}x}\right)$$

$$\approx \sum_n a_n f'_n t_n e^{2\pi i \frac{n}{p}\chi}$$

When the object to be detected is placed in the optical path, it causes phase shift $\phi(x)$ of X-ray, an image formed by the object and the grating G1 at the position of the grating G2 under the irradiation of X-ray is represented by the function $J_s(x)$, namely $$J_s(x) = J_1(x) * S(x) \quad (4)$$

Wherein $J_1(x)$ is the image of the object and the grating G1 at the position of the grating G2 under the condition of a point source, namely $$J_1(x) = \sum_n a'_n e^{2\pi i \frac{n}{p}[x+D\varphi(x)]}$$

Thus the light intensity curve function (named sample displacement curve) obtained in the detector unit is $$J_D(x, \chi) = J_s(x, \chi)T_2(x) \quad (5)$$

$$= [J_1(x) * S(x+\chi)]T_2(x)$$

$$= \left[\left(\sum_n a'_n e^{2\pi i \frac{n}{p}[x+D\varphi(x)]}\right) * \left(\sum_m f'_m e^{2\pi i \frac{m}{p}[x+\chi]}\right)\right]$$

$$\left(\sum_k t_k e^{2\pi i \frac{n}{p}x}\right)$$

$$\approx \sum_n a'_n f'_n t_n e^{2\pi i \frac{n}{p}[\chi+D\varphi(x)]}$$

The following contents prove that the source grating stepping technology and the technology of relative stepping of two absorption gratings lead to equivalent results.

Assume that the grating G2 performs stepping relative to G1, the displacement distance is $\chi$, the light intensity curve function obtained in the detector unit is:

the background displacement curve under the condition that the object to be detected is absent in the optical path:

$$I'_D(x, \chi) = I_s(x)T_2(x, \chi) \quad (6)$$

$$= [I_1(x) * S(x)]T_2(x+\chi)$$

$$= \left[\left(\sum_n a_n e^{2\pi i \frac{n}{p}x}\right) * \left(\sum_m f'_m e^{2\pi i \frac{m}{p}x}\right)\right]$$

$$\left(\sum_k t_k e^{2\pi i \frac{n}{p}(x+\chi)}\right)$$

$$\approx \sum_n a_n f'_n t_n e^{2\pi i \frac{n}{p}\chi}$$

the sample displacement curve under the condition that the object to be detected is present in the optical path:

$$J'_D(x, \chi) = J_s(x)T_2(x+\chi) \quad (7)$$

$$= [J_1(x) * S(x)]T_2(x+\chi)$$

$$= \left[\left(\sum_n a'_n e^{2\pi i \frac{n}{p}[x+D\varphi(x)]}\right) * \left(\sum_m f'_m e^{2\pi i \frac{m}{p}x}\right)\right]$$

$$\left(\sum_k t_k e^{2\pi i \frac{n}{p}(x+\chi)}\right)$$

$$\approx \sum_n a'_n f'_n t_n e^{2\pi i \frac{n}{p}[\chi+D\varphi(x)]}$$

It can be found upon comparison that the formulas (3) and (6) are equivalent, and formulas (5) and (7) are equivalent.

If the deduction is made based on an example of coherent X-ray imaging, wherein the distance between the first and second gratings G1, G2 is $D_T$, the result would be the same, only D in the formulas needs to be replaced by $D_T$. In addition, if it is under the coherent condition and the Talbot-Lau interference method is used, there exists such a relation:

$$p_2 = (p_1/2)*L/(L-D_T).$$

Accordingly, it can be summarized that the source grating stepping technology obtains a result substantially identical with that obtained by the technology of relative stepping of the first and second gratings, but meanwhile, it greatly reduces the precision requirement and difficulty in stepping and significantly enhancing the stability of the system.

CT Information Extraction and CT Image Reconstruction

During the X-ray imaging process of source grating stepping, the background displacement curve and sample displacement curve can be obtained for each detector unit (pixel) by means of the source grating stepping. In consideration of the limited sizes of the three gratings in the actual system, the background displacement curve and sample displacement curve are similar to a sinusoidal curve, namely $$I_s(k) \approx a_s + b_s \cos(k\Delta x + \phi_s) \quad (8)$$

$$I_b(k) \approx a_b + b_b \cos(k\Delta x + \phi_b) \quad (9)$$

wherein $I_s(k)$ and $I_b(k)$ are values of light intensity measured at step k in the presence of the sample and in the absence of the sample, $\Delta\chi$ is the step length, the phase change of the curve is $\Delta\phi = (\phi_s - \phi_b)$, and $a_s$, $a_b$, $b_b$ are sinusoidal curve coefficients. What is shown in FIG. 3 is the background displacement curve measured by an actual system. Wherein it can be predicted that the light intensity curve in the absence of the detected sample can serve as the background information, said information can be prestored in the storage of the system, or automatically obtained temporarily when the device starts.

Figure 5:
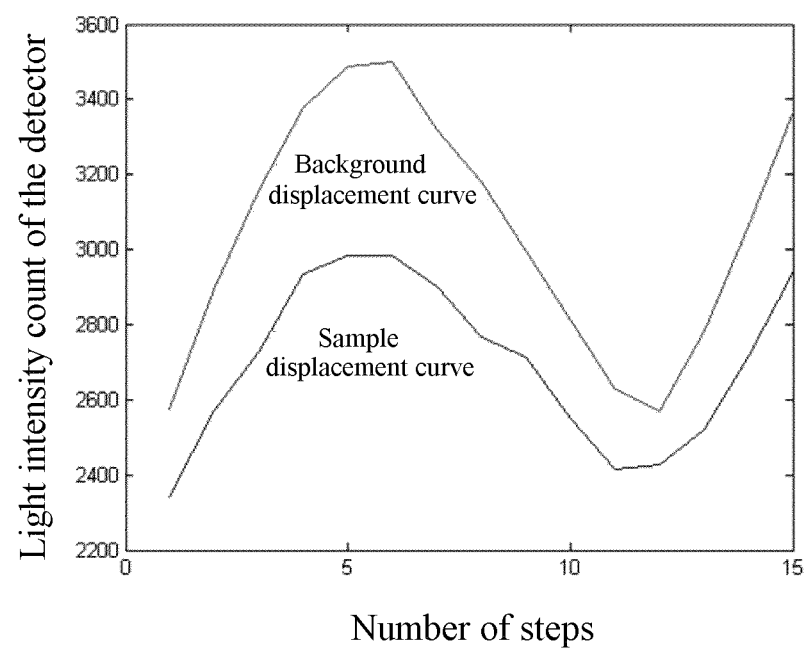
FIG. 5 shows a schematic diagram of X-ray intensity, contrast and phase change embodied by background displacement curve and sample displacement curve detected by a certain pixel of the detector after the X-ray passes through the object to be detected.

By comparison of the background displacement curve with sample displacement curve, as shown in FIG. 5, when the number of steps is relatively large (e.g. larger than or equal to 5, the more the number of steps is, the better the effect of picture composition would be), the following formulas can be used for calculating an attenuation value P (corresponding to an attenuation image), refraction angle value $\Delta\theta$ (corresponding to a phase contrast image) and a scattering angle distribution secondary moment $\sigma^2$ (corresponding to a dark field image) of the detector unit:

$$P = \int_l \mu(l)\,dl = -\ln\left(\frac{\sum_k I_s(k)}{\sum_k I_b(k)}\right) \quad (10)$$

$$\Delta\theta = \int_l \nabla \delta(l)\,dl = \frac{p_2 \Delta\phi}{2\pi D} \quad (11)$$

$$\sigma^2 = \int_l f_s(l)\,dl = -\frac{1}{2\pi^2}\left(\frac{p_2}{D}\right)^2 \ln\left(\frac{V_s}{V_b}\right) \quad (12)$$

wherein $\mu$ is a linear attenuation coefficient, $\delta$ is a refractive index phase factor, $f_s$ is a general scattering parameter, and l is a light propagation path. $V_s$ and $V_b$ are visibilities of the sample displacement curve and the background displacement curve, respectively. Wherein $I_{max}$ and $I_{min}$ respectively represent the maximum and minimum values of the light intensity curve, which shall have the following relationship:

$$V = \frac{I_{max} - I_{min}}{I_{max} - I_{min}}.$$

Of course, the number of steps may also be relatively small in order to simplify the setting. Particularly, in the source grating stepping technology, when the number of steps is less than 5, the way of solving equations may be used for calculating various information values. There already exist common deduction processes in the prior art, and the image effect thereof is always worse than that in the case of relatively large number of steps. Provided that $I_R$ is an intensity of X-ray after passing through the object, I is an intensity of X-ray after passing through the grating, $R_t(x)$ is a normalized background displacement curve function, and $f(\theta)$ represents a probability density distribution function after the X-ray is scattered by the object, they have the following relationship $$I = \int I_R R_t(x) f(\theta)\,d\theta \quad (13)$$

wherein $R_t(x) = A \sin(kx+\phi) + R_0$.

Wherein, when the number of steps is 2, 3 or 4 respectively, namely the stepping points are 2, 3 or 4 special position points respectively, a first-order, second-order or third-order Taylor's approximation expansion can be respectively performed for $R_t(x)$ and then put into the formula (13) to obtain approximation formulas respectively for the number of steps of 2, 3 or 4; and then images acquired at corresponding positions are put into the approximation formulas to calculate various information.

Particularly, when the number of steps is 2, for example, two special position points $kx=0, \pi$ are selected, images (represented for example by $I_1, I_2$) at the two positions can be used to calculate apparent absorption information $I_R$ and phase contrast information (viz. the refraction angle information) $\Delta\theta$:

$$I_R = \frac{I_1 + I_2}{2R_0} \quad (14)$$

$$\Delta\theta = \frac{p_2 R_0}{2\pi DA} \frac{I_1 - I_2}{I_1 + I_2} \quad (15)$$

More particularly, when the number of steps is 3, for example, three special position points are selected, the apparent absorption information $I_R$, phase contrast information $\Delta\theta$ and scattering information $\sigma^2$ are obtained by using images at these three positions and performing a second-order Taylor expansion for the displacement curves.

In the case of the relatively small number of steps, obtaining more image data than the number of steps leads to discrete distortion of image data, but also has the advantage of making the operation simple According to formulas (10) and (12), traditional filtered back projection algorithms (such as RL filtering, SL filtering) may be used to reconstruct a three-dimensional distribution of linear attenuation coefficient $\mu$ and general scattering parameter $f_s$ inside the object. Formula (10) indicates that the absorption and attenuation information of the detected object can be obtained by measuring change in the light intensity of X-ray passing through a certain point. Formula (12) indicates that the scattering information of the detected object can be indirectly measured by measuring change in the contrast of the X-ray intensity curves.

According to formula (11), Hilbert-filter based filtered back projection algorithms may be used to reconstruct a three-dimensional distribution of the refractive index (or the gradient thereof). Formula (11) indicates that the refraction information of the detected object can be indirectly obtained by measuring and calculating phase change $\Delta\phi$ in the displacement curve.

Figure 4:
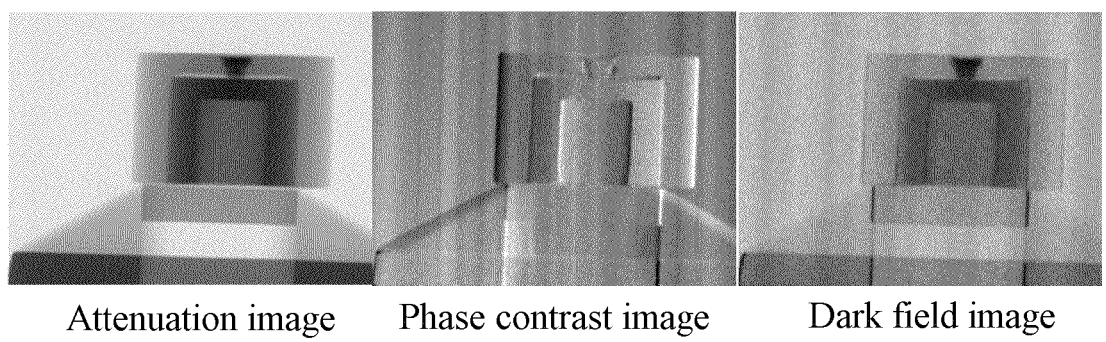
FIG. 4 shows a plurality of information images of a certain detected object as acquired by the imaging system of the present invention, wherein the left part of FIG. 4 is an absorption diagram, the middle part thereof is a phase-contrast diagram, and the right part thereof is a dark-field diagram.

The above-mentioned filtered back projection algorithms, for example, are well known to those skilled in the art, and the contents thereof are recited in quite a lot of documents, thus they would not be set forth here in detail and only the technical effects thereof would be stated. Actually, other similar algorithms may also be adopted. As FIG. 4 shows, 4a, 4b and 4c are attenuation image, phase contrast image and dark field image of the detected object, respectively, wherein the source grating has a period of 110 microns, a step length of 10 microns, and acquires data at 11 points, the periods of two absorption gratings in the fixed grating module are 10 and 11 microns respectively, according to image data at the 11 points.

If CT data acquisition is performed for the object to be detected, namely the object to be detected is imaged relative to the imaging system at different angles, the attenuation image, phase contrast image and dark field image at different angles are obtained respectively. The object to be detected such as human body can be rotated, for example by 360°. In this way, an actuation means is required to enable the object to be detected to rotate relative to the entire system, which is usually an electromechanical rotation actuation structure and controlled by an control module.

Imaging Process

The X-ray source emits X-ray to the object at each angle. Meanwhile, the source grating G0 of the imaging system of the present invention accomplishes stepping movement of at least one period. During said process, the detector converts light intensity signals into digitally processable electrical signals which are subjected to data processing by the data processing unit. By comparing change in the light intensity curve at each pixel point on the detector, one or more of the attenuation value, scattering value and refraction value of the X-ray passing through the object to be detected can be obtained at the pixel unit on the detector. The object is then relatively rotated by an angle and repeats the above grating stepping movement to obtain one or more of the attenuation value, scattering value and refraction value of the X-ray passing through the object to be detected at said another angle. The above processes are repeated to obtain one or more of the attenuation value, scattering value and refraction value of the X-ray passing through the object to be detected at multiple angles. A CT reconstruction algorithm is used to construct one or more of the attenuation value, scattering value and refraction value into a CT image of the detected object.

In order to extract a precise image, the following system parameters shall be precisely measured or calibrated: the distance from the X-ray source to the rotational center of the framework, the distance from the source grating to the fixed grating module, the distance between the two gratings in the fixed grating module, the distance from the source to the detector, the periods of the gratings, etc. The framework for supporting the object to be detected and/or device system is popularly used in the prior art and certainly used in the present invention as required, but the contents thereof would not be set forth here in detail, those skilled in the art are able to adopt a suitable framework based on the common knowledge and the teaching of the present invention.

Although the present invention is preferably based on the description of the non-coherent X-ray source, the concept and the inventive principle of the present invention are also suitable for the grating imaging using a coherent X-ray source.

The X-ray imaging method of the present invention further improves the grating imaging technology such that it can greatly reduce the precision of grating stepping and alleviate difficulty in construction of the imaging system and cost thereof, thereby facilitating application and popularization of the novel grating imaging technology. The present invention has changed the stepping technology based high-precision gratings in the existing grating synthetical imaging technology; only a stepping technology based on low-precision, long-period source gratings is required to achieve the same image quality and effect.

One or more of the three imaging manners of X-ray absorption, phase contrast and dark field can be performed on the same set of systems, such that images that supplement one another can be obtained (as shown in FIG. 4). A plurality of data processing functions can be integrated in the computer workstation so as to achieve one or more of the above imaging manners. The grating dark-field imaging based on a non-coherent X-ray source can be applied in the field such as material science, medical imaging of tissues (such as galactophore).

It shall be noted that those skilled in the art can design a lot of optional examples without deviating from the scope of the claims as enclosed. In the claims where several means are enumerated, several of the means can be implemented by the same hardware. The fact that some measures are only stated in the dependent claims that are different from one another does not indicate that the combination of these measures cannot be advantageously used.

The invention claimed is:

1. An X-ray imaging system for imaging an object using X-ray, said system comprises: an X-ray source (S), a source grating (G0), a fixed grating module (P) and an X-ray detector (T), which are successively positioned in the propagation direction of the X-ray; an object to be detected is positioned between the source grating and the fixed grating module;

said source grating can perform stepping movement in a direction perpendicular to the optical path direction and grating stripes;

wherein said system further comprises a computer workstation; said system is adapted for accomplishing the following processes:

said source grating performs stepping movement in at least one period thereof;

at each stepping step, the X-ray source emits X-ray to the object to be detected, and the detector receives the X-ray at the same time; wherein after at least one period of stepping and data acquisition, the light intensity of X-ray at each pixel point on the detector is represented as a light intensity curve;

the light intensity curve at each pixel point on the detector is compared with a light intensity curve in the absence of the object to be detected, a pixel value of each pixel point is calculated from change in said light intensity curve;

an image of the detected object is reconstructed according to the calculated pixel value.

2. The system according to claim 1, wherein said system further comprises an actuation means for enabling said source grating to perform stepping movement and/or enabling said object to be detected to rotate by an angle relative to other portions of said system under the control of the computer workstation.

3. The system according to claim 2, wherein said source grating stepping process is repeated at each rotation angle, thereby obtaining pixel values of X-ray imaging at multiple angles, and a stereo image of the object to be detected is then reconstructed according to a predetermined CT image reconstruction algorithm.

4. The system according to claim 1, wherein said computer workstation comprises:

a data processing module for processing data information and calculating pixel values of respective points on the object to be detected therefrom;

an image reconstruction module for reconstructing an image of the object to be detected according to the calculated pixel values; and a control module for controlling operations of said X-ray source, source grating, and X-ray detector.

5. The system according to claim 1, wherein said fixed grating module (P) comprises relatively fixed first and second gratings (G1, G2).

6. The system according to claim 1, wherein said computer workstation further comprises a display unit for displaying an image of the object to be detected.

7. The system according to claim 1, wherein said computer workstation is capable of calculating refraction information of X-ray at a predetermined point on the object to be detected upon comparison between the light intensity curve in the presence of the object to be detected and the background light intensity curve in the absence of the object to be detected, and calculating a corresponding pixel value therefrom.

8. The system according to claim 1 wherein said computer workstation is capable of calculating scattering information of X-ray at a predetermined point on the object to be detected upon comparison between the light intensity curve in the presence of the object to be detected and the background light intensity curve in the absence of the object to be detected, and calculating a corresponding pixel value therefrom.

9. The system according to claim 1 wherein said computer workstation is capable of calculating attenuation information of X-ray at a predetermined point on the object to be detected upon comparison between the light intensity curve in the presence of the object to be detected and the background light intensity curve in the absence of the object to be detected, and calculating a corresponding pixel value therefrom.

10. The system according to claim 1, wherein said X-ray source emits non-coherent X-ray.

11. The system according to claim 5, wherein said source grating, first and second gratings G1 and G2, and X-ray detector have the following relationship:

$$\frac{p_1}{p_2} = \frac{L}{L+D}$$

wherein, $p_1$ and $p_2$ are periods of the first and second gratings (G1, G2) respectively, L is a distance between the X-ray source and the first grating (G1), and D is a distance between the first and second gratings.

12. The system according to claim 5, wherein said source grating, first and second gratings G1 and G2, and X-ray detector have the following relationship:

$$p_2 = (p_1/2) * L/(L-D_T)$$

wherein, $p_1$ and $p_2$ are periods of the first and second gratings (G1, G2) respectively, L is a distance between the X-ray source and the first grating (G1), $D_T$ is a distance between the first and second gratings, and $D_T = p_1^2/(8\lambda)$, and $\lambda$ is a wavelength of X-ray.

13. An X-ray imaging method for imaging an object by means of an X-ray imaging system, wherein said X-ray imaging system comprises: an X-ray source, a source grating, a fixed grating module, an X-ray detector and a computer workstation;

wherein said method comprises performing the following steps under the control of the computer workstation:

emitting X-ray to the object to be detected;

enabling the source grating to perform stepping movement in at least one period;

at each stepping step, the X-ray detector receiving X-ray and converting it into processable digital electrical signals; wherein after at least one period of stepping and data acquisition, the light intensity of X-ray at each pixel point on the detector is represented as a light intensity curve;

comparing the light intensity curve at each pixel point on the detector with a light intensity curve in the absence of the object to be detected, thereby obtaining change in the light intensity curve;

calculating a pixel value of each pixel point from change in said light intensity curve; and an image reconstruction module reconstructing an image of the detected object according to all pixel values.

14. The method according to claim 13, wherein said computer workstation comprises: a control module, a data processing module and an image reconstruction module.

15. The method according to claim 13, further comprising: rotating the object to be detected, repeating said respective steps at each rotation angle to obtain a distribution of pixel values of respective points of the object to be detected on the X-ray detector at different angles, and then reconstructing a stereo image of the object to be detected according to a CT image reconstruction algorithm.

16. The method according to claim 13, further comprising: calculating refraction information of X-ray at a predetermined point on the object to be detected upon comparison between the light intensity curve in the presence of the object to be detected and the background light intensity curve in the absence of the object to be detected, and calculating a corresponding pixel value therefrom.

17. The method according to claim 13 further comprising: calculating scattering information of X-ray at a predetermined point on the object to be detected upon comparison between the light intensity curve in the presence of the object to be detected and the background light intensity curve in the absence of the object to be detected, and calculating a corresponding pixel value therefrom.

18. The method according to claim 13 further comprising: calculating attenuation information of X-ray at a predetermined point on the object to be detected upon comparison between the light intensity curve in the presence of the object to be detected and the background light intensity curve in the absence of the object to be detected, and calculating a corresponding pixel value therefrom.

19. The method according to claim 18, wherein said computer workstation further comprises a display unit for displaying an image of the detected object, said method further comprising:

complementally displaying the reconstructed images.

20. The method according to claim 18, wherein the stepping process includes that the stepping number in one period of the source grating is more than 5.

21. The method according to claim 18, wherein the stepping process includes that the stepping number in one period of the source grating is less than 5.

22. A computer program product comprising computer executable instructions for achieving the method according to claim 13.

* * * * *